United States Patent [19]

Geyer et al.

[11] Patent Number: 5,110,606
[45] Date of Patent: May 5, 1992

[54] NON-AQUEOUS MICROEMULSIONS FOR DRUG DELIVERY

[75] Inventors: Robert P. Geyer, Brookline, Mass.; Vinod Tuliani, Media, Pa.

[73] Assignee: Affinity Biotech, Inc., Boothwyn, Pa.

[21] Appl. No.: 612,592

[22] Filed: Nov. 13, 1990

[51] Int. Cl.⁵ .................... A61K 9/10; A61K 9/101
[52] U.S. Cl. .................... 424/489; 424/502; 514/165; 514/937; 514/943; 514/557; 514/396
[58] Field of Search ............... 424/489; 514/570, 960, 514/937, 941

[56] References Cited

U.S. PATENT DOCUMENTS 4,851,444  7/1989  Sunshine et al. .................... 514/570

OTHER PUBLICATIONS

The Merck Index, Tenth Edition, Merck & Co., Inc. 1988; pp. 1372; 1130-1131; 1092; 644.

Primary Examiner—Thurman K. Page
Assistant Examiner—Raj Bawa
Attorney, Agent, or Firm—Woodcock Washburn Kurtz Mackiewicz & Norris

[57] ABSTRACT

Palatable liquid therapeutic microemulsion wherein a drug dissolved in propylene glycol is dispersed in fatty ester. Lecithin is the emulsifier.

7 Claims, No Drawings

NON-AQUEOUS MICROEMULSIONS FOR DRUG DELIVERY

BACKGROUND OF THE INVENTION

Liquid administration of drugs is convenient and often advantageous, especially when dealing with children or the elderly for whom pill swallowing can be difficult or even hazardous. Unfortunately, many drugs are not soluble in water, while water solution of others such as ibuprofen may have a very unpleasant taste. Some drugs, such as aspirin, are either unstable in the presence of water or are insoluble in water and therefore cannot be incorporated into aqueous formulations. To overcome these various problems a water-free liquid preparation of a number of drugs would be desirable.

SUMMARY OF THE INVENTION

The invention is a nonaqueous emulsion useful for drug delivery which largely overcomes the problems mentioned above with water-unstable and/or unsavory drugs. For example, use of the invention, a very palatable ibuprofen formulation can be made in which only one teaspoon contains a normal child's dose.

The emulsion contains a drug dissolved in a suitable non-aqueous internal phase solvent, such as propylene glycol, dispersed, with a suitable emulsifier such as lecithin in an alkyl fatty acid ester. Excipients such as sweeteners, flavoring agents and taste masking materials can also be included.

A key feature of the invention is its ability to prevent the crystallization of the drug from the internal phase, even when the level of drug in that phase is above saturation levels.

DETAILED DESCRIPTION OF THE INVENTION

The nonaqueous, internal phase of the emulsion is a polar, pharmaceutically-acceptable oxygen-containing liquid such as $C_2$-$C_{30}$, preferably $C_2$-$C_{20}$ polyhydric alcohols, poly(ethylene or propylene) glycols with 4-200 repeating units, and the $C_1$-$C_5$ ether or $C_2$-$C_{30}$, preferably $C_2$-$C_{20}$ ester derivatives of any of the foregoing. Examples of such materials include glycerin, propylene glycol, polyethylene glycol 200, 400, 600, 1500, 4000 and 6000 with the number correlating approximately with the number of repeating units and ranging from 4 to 200, ethylene glycol dimethyl ether, tetraethylene glycol dimethyl ether, triacetin, medium chain ($C_6$-$C_{10}$) triglycerides such as tricaprylin (caprylic acid ester of glycerol, and propylene glycol $C_8$ diester (Captex 200). Preferably the internal phase is a $C_2$-$C_{10}$ polyhydric alcohol, a polyethylene glycol with n=4-80, or the methyl or ethyl ethers thereof.

The drug is dissolved in the internal non-aqueous phase. By drug is meant any therapeutic agent such as hormones, vitamins, enzymes, drugs, etc. Typical drugs which are suitable include aspirin, ibuprofen, piroxicam, cimetidine, fat soluble vitamins and steroids such as estrogen and vitamins A, D and E. Preferably the drug is aspirin, ibuprofen, or cimetidine. In addition, other water sensitive compounds such as aspartame would have increased stability in such non-aqueous systems.

One of the key advantages of our invention is that the non-aqueous solution of the drug can be supersaturated. The solvent is heated to about 80° C., i.e., a temperature at which about 2-4 times or more the amount of drug that would form a saturated solution at room temperature is dissolved in the solvent. When such solutions are cooled to room temperature the drug ordinarily would crystallize out; however, once incorporated into the microemulsion, it remains as a supersaturated solution.

The emulsion also contains lecithin as the emulsifier. Egg or soya lecithin is suitable. Lecithin itself is a solid but is also available commercially as a liquid by having been mixed with oil such as soybean oil. These liquid lecithins are suitable and, indeed, are preferred. Attempts to accomplish the same liquefying effect by using some of our lower alkyl fatty ester have resulted in slightly cloudy emulsions, but we think this is merely a matter of technique.

The continuous phase of the emulsion is a lower alkyl ester of a $C_8$-$C_{22}$ fatty acid such as ethyl palmitate or a triglyceride. The alkyl is $C_{1-5}$ preferably $C_{1-3}$. Monoesters are preferred because di or triesters such as soybean oil tend to be more oily in taste and texture, although even this can be masked.

Sweeteners such as saccharin, aspartame (depending on the temperature used in preparation), sorbitol, corn syrup, etc. and other taste maskers such as the oils of peppermint and sweet orange, clove, cherry syrup, etc. can be included in the formulation. These agents can be added to any one or more of the components of the emulsion to insure their effectiveness throughout the whole emulsion.

The relative amount of the ingredients in the formulation will vary but is generally as follows, with all percentages being volume percentages unless otherwise noted.

The continuous phase, including any used as lecithin vehicle, predominates relative to the internal phase and is usually 33-70% with the internal phase being 1-20%. The actual lecithin, i.e., excluding vehicle, will be 20-60%. Preferably the continuous phase is 40-65%, the internal phase 5-20%, and the actual liquid lecithin 25-45%.

The drug is usually 0.1-15 weight percent of the drug-internal phase solution. Masking agents, when used, will usually be less than three percent, preferably 0.1-2 percent.

Our emulsion is a microemulsion. It forms spontaneously with gentle mixing such as hand shaking. High shear mechanical mixing devices are not required. In addition, the emulsion is clear and looks and acts as a single phase. It is stable indefinitely and this stability is evident up to at least 45° C., well above any temperature likely to be encountered between manufacture and use.

The following describes the preparation of an emulsion typical of our invention, in which the term volume refers to microliters.

Ibuprofen is dissolved in hot, 80° C., 1,2-propylene glycol to make a 30.8 wt. % solution. 95 volumes of this hot ibuprofen solution is mixed with 450 volumes of room temperature lecithin. The latter is "Centrophase 31" special soybean (food grade) from Central Soya Company to which has been added 0.6 wt. % aspartame. This lecithin is 60-64% soya lecithin (acetone insolubles), the balance being essentially soybean oil. It is liquid.

The mixture is immediately gently hand mixed at room temperature by means of a stirring rod. After five minutes a clear preparation forms. Its spontaneous formation indicates a glycol-lecithin soybean oil microemulsion but this is not, in this case, our final product.

When certain applications require the use of this first microemulsion, the formulation can be stopped at this point. Stirring continues for another five minutes as 5 volumes oil of sweet orange are added. Stirring continues for another ten minutes as 450 volumes ethyl palmitate are stirred in. A final microemulsion (179185) of the ibuprofen-propylene glycol soybean oil phase in the fatty ester is obtained. The final microemulsion is clear, stable, and behaves as a solution.

It is to be noted in the above procedure that even though the glycol contains about four times as much ibuprofen as could be dissolved at room temperature, no ibuprofen crystallizes out of the glycol solution when the latter is mixed with the lecithin. If the glycol is cooled to room temperature before mixing with the lecithin, ibuprofen crystals do appear. In any event, having both the glycol and lecithin hot before mixing is better practice, even though the above shows it is not always necessary, and may even be required at higher drug concentrations.

The emulsion prepared above is sweet tasting with an agreeable quality or feel. It contains 140 milligrams ibuprofen (a child's dose) in five milliliters of emulsion, the latter being equal to one teaspoon. Without the supersaturation of the glycol, the dosage would be greater than a tablespoon and much more difficult to administer to a child. With higher supersaturation of the glycol the dosage would be less than a teaspoon and would be even more easy to administer to a child.

Another emulsion (179162) was made in essentially the same manner except that the internal phase was 90 volumes of a propylene glycol solution containing 37.5% (wt) ibuprofen and 0.3% aspartame to which is then added 10 volumes clove oil. The emulsifier was 450 volumes "Centrophase 31" to which was added 10 volumes clove oil. Finally, the ethyl palmitate (450 volumes) contained 0.3% aspartame and 10 volumes added clove oil. The results are essentially the same with respect to emulsion formation and emulsion quality.

The same results are also obtained in making an emulsion (179157) in which the internal phase is 90 volumes of a 23.8 wt. % solution of cimetidine in propylene glycol which is added to 450 volumes Centrophase 31 lecithin. After the first emulsion of these components forms excipients aspartame (0.3 wt. % overall) 7.5 volumes cherry flavor and 2.5 volumes vanilla flavor are added. The external phase is 450 volumes ethyl palmitate.

Finally, an emulsion (179183) is made the same way as above with an internal phase of one volume of a 20% aspirin solution (wt.) in triacetin. 4.5 volumes of the sam lecithin and 4.5 volumes ethyl palmitate are used. The results are substantially the same as above. In this example the term volumes refers to milliliters.

The invention claimed is:

1. An emulsion composition comprising as internal phase, a drug contained in a polar, nonaqueous oxygen-containing, pharmaceutically acceptable liquid selected from the group consisting of glycerin, propylene glycol, polyethylene glycol 200, 400, 600, 1500, 4000 and 6000, ethylene glycol dimethyl ether, tetraethylene glycol dimethyl ether, triacetin, medium chain ($C_8$–$C_{10}$) triglycerides and propylene glycol $C_8$ diester, said internal phase being dispersed in a lower alkyl ester of a $C_8$–$C_{22}$ fatty acid external phase, and lecithin as emulsifying agent, the amounts of the components being polar liquid, 1–20%; fatty ester, 33–70%; and lecithin 20–60%.

2. Emulsion according to claim 1 wherein said amounts are 5–20%, 40–65%, and 25–45% respectively.

3. Emulsion according to claims 1 or 2 wherein said drug is aspirin or ibuprofen.

4. Emulsion according to claims 1 or 2 wherein said fatty ester is ethyl palmitate.

5. Emulsion according to claims 1 or 2 wherein said internal phase is a supersaturated solution of said drug.

6. Emulsions according to claims 1 or 2 wherein said drug is ibuprofen, aspirin or cimetidine.

7. Emulsion according to claims 1 or 2 wherein said internal phase is a polyhydric alcohol.

* * * * *